United States Patent
Maizes (10) Patent No.: US 9,622,719 B2
(45) Date of Patent: Apr. 18, 2017

(54) COLOR ULTRASOUND NEEDLE

(71) Applicant: Allen Maizes, Scotch Plains, NJ (US)

(72) Inventor: Allen Maizes, Scotch Plains, NJ (US)

( * ) Notice: Subject to any disclaimer, the term of this patent is extended or adjusted under 35 U.S.C. 154(b) by 385 days.

(21) Appl. No.: 14/178,984

(22) Filed: Feb. 12, 2014

(65) Prior Publication Data

US 2014/0243657 A1   Aug. 28, 2014

Related U.S. Application Data

(60) Provisional application No. 61/769,300, filed on Feb. 26, 2013.

(51) Int. Cl.
| | |
|---|---|
| *A61B 8/00* | (2006.01) |
| *A61B 8/08* | (2006.01) |
| *A61M 5/32* | (2006.01) |
| *A61B 17/34* | (2006.01) |
| *A61M 5/42* | (2006.01) |
| *A61B 90/00* | (2016.01) |

(52) U.S. Cl.
CPC ............ *A61B 8/0841* (2013.01); *A61B 8/488* (2013.01); *A61M 5/32* (2013.01); *A61B 8/461* (2013.01); *A61B 2017/3413* (2013.01); *A61B 2090/3925* (2016.02); *A61M 5/427* (2013.01)

(58) Field of Classification Search
CPC ....... A61B 8/00; A61B 8/0833; A61B 8/0841; A61B 8/463; A61B 8/481; A61B 8/483; A61B 2019/5433
See application file for complete search history.

(56) References Cited

U.S. PATENT DOCUMENTS

| | | | |
|---|---|---|---|
| 4,401,124 A | 8/1983 | Guess et al. | |
| 4,428,379 A | 1/1984 | Robbins et al. | |
| (Continued) | | | |

FOREIGN PATENT DOCUMENTS

| | | |
|---|---|---|
| EP | 0083973 A1 | 7/1983 |
| EP | 0453251 A1 | 10/1991 |
| (Continued) | | |

OTHER PUBLICATIONS

"The Echogenic EchoTuohy Epidural Needle for Ultrasound Guided Injections & Catheter Placement", http://www.havels.com, http://www.havels.com/echotuohy.html (Accessed Sep. 29, 2023).

(Continued)

*Primary Examiner* — Joel Lamprecht
(74) *Attorney, Agent, or Firm* — Barlow, Josephs & Holmes, Ltd.

(57) ABSTRACT

An echogenic needle and a method of using the needle with an ultrasound machine, in which the needle has a turbulence inducing member positioned within the hollow body of the needle towards the tip end of the needle. The turbulence inducing member is preferably be a reamer. When fluid media passes through the flow path in the hollow body of the needle, the needle induces turbulent flow in the fluid exiting the tip of the needle. This turbulent flow is visible in color on an output display of the ultrasound machine using a color Doppler feature, and is helpful for determining the location of the tip of the needle in an image on the ultrasound display. The tip of the needle may be beveled or blunt. The turbulence inducing member may partially extend from the distal end of the needle and may be of different configurations.

13 Claims, 6 Drawing Sheets

(56) References Cited

U.S. PATENT DOCUMENTS

| | | | |
|---|---|---|---|
| 4,431,006 A | 2/1984 | Trimmer et al. | |
| 4,977,897 A | 12/1990 | Hurwitz | |
| 5,095,910 A | 3/1992 | Powers | |
| 5,343,865 A | 9/1994 | Gardineer et al. | |
| 5,383,466 A | 1/1995 | Partika | |
| 5,490,521 A | 2/1996 | Davis et al. | |
| 5,549,112 A | 8/1996 | Cockburn et al. | |
| 5,820,554 A | 10/1998 | Davis et al. | |
| 6,018,676 A | 1/2000 | Davis et al. | |
| 6,053,870 A | 4/2000 | Fulton, III | |
| 8,369,935 B2 | 2/2013 | Ryan | |
| 8,430,863 B2 | 4/2013 | Webler | |
| 8,968,210 B2* | 3/2015 | Mugan | A61B 10/0283 600/562 |
| 2006/0293592 A1* | 12/2006 | Jensen | 600/424 |
| 2007/0197954 A1* | 8/2007 | Keenan | A61B 8/0833 604/20 |
| 2007/0293724 A1 | 12/2007 | Saadat et al. | |
| 2008/0287801 A1* | 11/2008 | Magnin | A61B 8/0833 600/463 |
| 2009/0118612 A1 | 5/2009 | Grunwald et al. | |
| 2009/0177114 A1 | 7/2009 | Chin et al. | |
| 2010/0305432 A1 | 12/2010 | Duhay et al. | |
| 2010/0312117 A1 | 12/2010 | Fernandez et al. | |
| 2012/0095404 A1 | 4/2012 | Massengale et al. | |
| 2012/0123249 A1 | 5/2012 | Kim et al. | |
| 2012/0130414 A1 | 5/2012 | Birkill et al. | |

FOREIGN PATENT DOCUMENTS

| | | |
|---|---|---|
| EP | 1132049 A1 | 9/2001 |
| GB | 2287319 A | 9/1995 |
| JP | 8206118 A | 8/1996 |
| JP | 118940 A | 4/1999 |
| JP | 2011125632 A | 6/2011 |
| WO | 2004082749 A2 | 9/2004 |
| WO | 2006046029 A2 | 5/2006 |

OTHER PUBLICATIONS

Tsui, Ban MSc, MD; Leipoldt, Carl MB, ChB; Desai, Sunil MB, ChB, "Color Flow Doppler Ultrasonography Can Distinguish Caudal Epidural Injection from Intrathecal Injection", http://europepmc.org/abstract/MED/23558836 (Accessed Oct. 16, 2013).

Harmat, A., Rohling, R. N., Salcudean, S. E., "Needle tip localization using stylet vibration", www.umbjournal.org, http://www.umbjournal.org/article/S0301-5629%2806%2901632-2/abstract (Accessed Oct. 16, 2013).

"Needle Visualization in Ultrasound-Guided Regional Anesthesia: Challenges and Solutions", www.sciencedirect.com, http://www.sciencedirect.com/science/article/pii/S1098733908001570 (Accessed Oct. 16, 2013).

* cited by examiner

COLOR ULTRASOUND NEEDLE

CROSS REFERENCE TO RELATED APPLICATION

This application is related to and claims priority from earlier filed provisional patent application Ser. No. 61/769,300, filed Feb. 26, 2013, titled "COLOR ULTRASOUND NEEDLE," the entire contents of which is incorporated herein by reference.

BACKGROUND OF THE INVENTION

The invention relates generally to the insertion of needles into tissue. Generally, physicians use medical ultrasound machines to visualize where to place a needle into tissue. The needle may be placed either into blood vessels, near nerves, into amniotic fluid, or for chorionic villus sampling as examples.

There is a need in medicine to know the location of the needle during its insertion into tissue to properly locate the needle where desired and to avoid placement of the needle where it may cause unwanted damage.

There is a known problem in the prior art that the needle may or may not be difficult to visualize using ultrasound. For example, the degree of obesity of a patient, varied anatomy of patients, and different practitioner's skill levels affect needle visualization. The ultrasound gives us pictures that are black and white, or gray scale.

The use of regional anesthesia is becoming increasingly popular, as it is associated with less blood loss, less blood clots, less stress hormones produced for surgery, decreased recovery times, less post-operative pain, and less nausea. However, administration of regional anesthetics can be a difficult skill to master, particularly for older generation physicians who have less familiarity with ultrasound devices.

There have been attempts in the prior art to make a needle more visible, such as laser etching the needle to make it more visible in black and white. However, even more visualization is desired.

There is a need for better visualization of the needle to achieve more accurate needle placement, avoiding injury to neighboring structures, and to allow more successful needle placement.

There is a need for the cost of an improved needle to be comparable to a standard needle.

There is a need for an improved needle that is meant for single patient use, namely, one that is disposable.

SUMMARY OF THE INVENTION

The present invention preserves the advantages of prior art ultrasound needles. In addition, it provides new advantages not found in currently available ultrasound needles and overcomes many disadvantages of such currently available ultrasound needles.

The exemplary embodiment of the present invention includes a modified needle, such as a Stimuplex A Insulated needle, manufactured by B.Braun. The needle is made to be visible in color by making turbulent flow through the needle using a mechanical turbulence inducing structure in the needle and using the color Doppler feature on the ultrasound machine for viewing it. Prior art needles are not capable of being visible in color because they do not induce turbulence that can be seen using the color Doppler feature of the ultrasound machine.

The flow through the needle can be changed thereby allowing the needle tip/fluid egress to be seen in color. As a result, the present invention allows ultrasound needle placement, such as location of the tip, to be successful even in difficult patient anatomy and with a minimally trained practitioner. A colored jet flow of fluid egress would allow easier visualization than possible with current needles.

A manufacturer provides a user (such as an anesthesiologist) with the echogenic needle of the present invention. In the preferred embodiment, the needle of the present invention is an insulated needle having a hollow body a substantially cylindrical outer profile, a proximal end, and a distal end. The hollow body of the needle defines a flow path through the needle so that a fluid can be directed from the proximal end of the needle to a tip of the needle located at the distal end of the needle. The proximal end of the needle is configured to engage medical tubing or a syringe. In the exemplary embodiment, the distal end of the needle has a beveled tip to improve the ability of the needle to pierce a user's skin. In other embodiments, the tip is formed as a blunt end.

A user is also provided with an ultrasound machine with a color display to show the output of the ultrasound machine using the color Doppler feature and to assist in proper location of the needle within a patient. When, media, such as fluid, in the form of water, saline or the like, is caused to flow through the needle from the proximal end towards the distal end and then out of the tip of the needle, it passes through or over a turbulence inducing member positioned within the flow path of the hollow body of the needle. In the exemplary embodiment, the turbulence inducing member is located proximal to the tip of the needle.

The turbulence inducing member may take various forms. In the preferred embodiment, the turbulence inducing member is a reamer. The fluted surfaces of the reamer create a helical path for the fluid within the hollow body of the needle. When the fluid exits the needle, it will have substantially turbulent flow within the region of the patient's body (or other tissue) into which it is injected. This substantially turbulent flow is visible as a 360° sphere by using the Doppler feature of the color ultrasound machine.

A manufacturer may provide a needle or a set of needles to a user along with an ultrasound machine or separately from the ultrasound machine.

The user activates the ultrasound machine, namely with the color Doppler feature enabled, and positions a transducer over a region of interest on a patient's body. The transducer is configured for use with a Doppler ultrasound machine with a color display. The transducer is capable of sending and receiving sound waves. Movement of the fluid within the tissue of the patient is detected by the Doppler ultrasound machine and displayed on the color display.

The user inserts the needle into the region and causes a fluid to pass through the flow path in the hollow body of the needle. The turbulence inducing member causes the fluid to have a turbulent flow immediately after it exits the needle. The user observes this turbulent flow as a bright color region on the output display of the ultrasound machine. The user can see both the anatomy of the patient (substantially in black and white or grayscale) and the bright area of turbulent flow (substantially in color) that is adjacent to the tip of the needle. The user moves the needle tip to a desired target location within the patient by adjusting the angle of the needle with respect to the patient's body and adjusting the depth of insertion of the needle within the patient's body while watching the output display of the ultrasound machine.

It is therefore an object of the present invention to provide better visualization of a needle to achieve more accurate needle placement by inducing turbulence at the tip of the needle and viewing it by an ultrasound machine using the Doppler feature.

Another object of the invention is to avoid injury to neighboring structures, and allow more successful needle placement.

It is an object of the present invention to keep the cost of an improved needle comparable to a standard needle.

A further object of the invention to provide a needle that is for single patient use and disposable.

BRIEF DESCRIPTION OF THE DRAWINGS

The novel features which are characteristic of the present invention are set forth in the appended claims. However, the invention's preferred embodiments, together with further objects and attendant advantages, will be best understood by reference to the following detailed description taken in connection with the accompanying drawings in which:

DETAILED DESCRIPTION OF THE PREFERRED EMBODIMENT

Referring now to the drawings, the color ultrasound needle of the instant invention is illustrated and generally indicated at 10. As will hereinafter be more fully described, the instant color ultrasound needle 10 provides an echogenic medical needle that delivers turbulent fluid such as medication or saline to a patient, whereby a doctor or other individual using the needle on the patient can determine the location of the tip of the needle within the patient by finding the location of the turbulent fluid on a color Doppler ultrasound display.

The present needle 10 assembly of the exemplary embodiment was achieved after experimentation with different baffling or screw tip designs, and wedged them into the tip of the needle. This lead to different fluid flow rates and turbulence at the needle tip. The exemplary embodiment in the figures is a preferred embodiment, with geometry for certain turbulence to allow for good color display on the ultrasound machine.

The present invention overcomes the problems in the prior art because it is much easier to see, such as in an obese patient. It is also easy to see for practitioners at any level of skill or training Instead of ultrasound visualization in black and white or grayscale, visualization in the present invention is in color using the Doppler feature of the ultrasound machine.

The present invention can modify a standard nerve block needle to induce turbulence in the fluid that exits the needle. The standard needle can be modified so that the first fluid molecule to exit the needle has sufficient velocity and turbulence so the first fluid to flow from the needle tip would be seen in color by the Doppler feature built into the ultrasound machine. The fluid directed through the needle can be a medication, an anesthetic, 0.9% saline, or another fluid.

Figure 1:
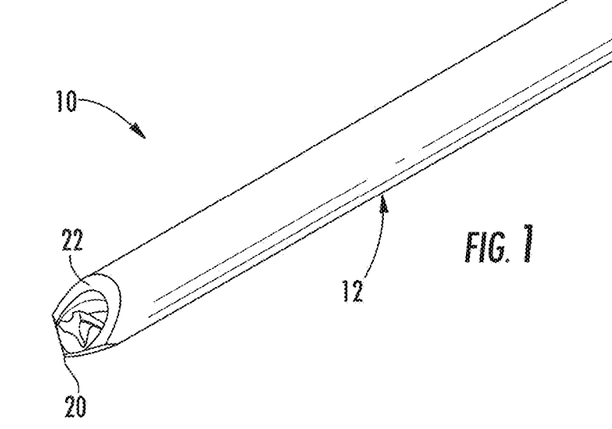
FIG. 1 is a perspective view of the needle assembly with internal reamer to create turbulent air flow.
Figure 2:
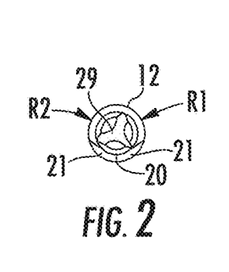
FIG. 2 is an end view of the needle with reamer residing therein.
Figure 3:
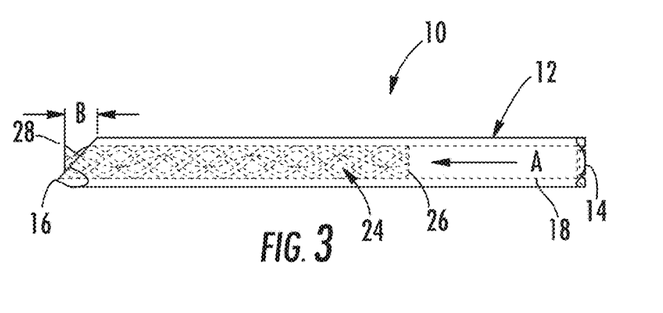
FIG. 3 is a side view of the needle assembly, with the internal structure shown in broken lines.

FIGS. 1-3 show the exemplary embodiment of the needle 10 of the present invention. The needle has a hollow body 12 that has a proximal end 14 and a distal end 16. When fluid is directed to a patient, it passes through a flow path 18 within the hollow body 12, from the proximal end 14 to the distal end 16, where the tip 20 of the needle is defined and located.

The tip 20 of the needle 10 of the embodiment of FIGS. 1-3 is preferably beveled, which is advantageous for piercing the skin of a user with minimal force. The bevel face 22 formed on the tip and the bevel angle can be designed according to user needs or preferences. Preferably, the bevel angle is in the range of 30° to 45° with respect to the longitudinal axis of the needle 10.

The present invention can be uniquely visible in color by the creation of turbulent flow at the needle tip so it can be easily seen. This can be carried out in many different ways using different structures. A turbulence inducing member 24 is positioned within the flow path, or adjacent to the distal end of the flow path.

In the exemplary embodiment, the turbulence inducing member 24 is a reamer that is located toward the distal end 16 of the hollow body 12. The reamer 24 has a proximal end 26 and a distal end 28, which are respectively aligned coaxially with the proximal end 14 and distal end 16 of the hollow body 12. In the exemplary embodiment, the reamer 24 is located adjacent to the tip 20 of the needle 10. While reamers are normally used as machining tools, here the helical flutes of the reamer are used to induce turbulent flow of the fluid passing thereover and therearound so that turbulent flow is visible around and about the tip of the needle when viewed with an ultrasound device.

FIG. 2 shows a view of the tip end of the needle 10, with both the hollow body 12 and the reamer 24 visible. This view shows that the lands 30 of the reamer 24 define an outer diameter of the reamer 24 that is substantially equal to the inner diameter of the hollow body 12 that defines the flow path 18 of the needle 10. Thus, fluid moving from the proximal end 14 to the distal end 16 of the hollow body 12 is directed in a substantially helical path along the flutes 32 of the reamer 24.

Together, FIGS. 1-3 show that the hollow body 12 of the needle 10 of the exemplary embodiment has a substantially cylindrical outer profile having a radius of R1 and a substantially cylindrical inner profile having a radius of R2. In the exemplary embodiment R1 is 0.018" and R2 is 0.012". This configuration is just one example of a turbulence inducing member 24 that can be used.

FIG. 3 shows a side view of the fully assembled needle 10 of the exemplary embodiment. The internal surface of the hollow body is shown in broken lines. This internal surface defines the flow path 18 of the hollow body 12. Fluid can be directed to a patient by moving it through the hollow body 12 along the arrow A. In the exemplary embodiment, when the turbulence inducing member 24 is not residing within the hollow body, the flow path 18 can be configured to provide substantially laminar flow of the fluid within the hollow body 12 in the direction A that is substantially parallel with the longitudinal axis of the hollow body 12.

Because the exemplary embodiment has a beveled tip, and because the reamer 24 has a flat face 29 at its distal end 28, the reamer partially extends beyond the bevel tip face 22 in FIG. 3 by a distance of B in the longitudinal direction. The distance B is measured from the flat face 29 of the distal end to of the reamer to the point on the bevel tip face 22 that is closest to the proximal end 14 of the hollow body 12. In the exemplary embodiment, the distance B is equal to 0.024". It is possible to position the reamer 24 closer to the proximal end 14 of the hollow body 12 of the needle 10. It is also possible to modify the geometry of the distal end of the reamer. The reamer 24 may extend outside the tip 20 or may be completely contained within the hollow body 12.

The bevel tip 20 of the needle may further include a lancet tip, with lancet surfaces 21 that come together to form a sharper tip 20 for piercing a patient's skin or other tissue.

Figures 4, 5:
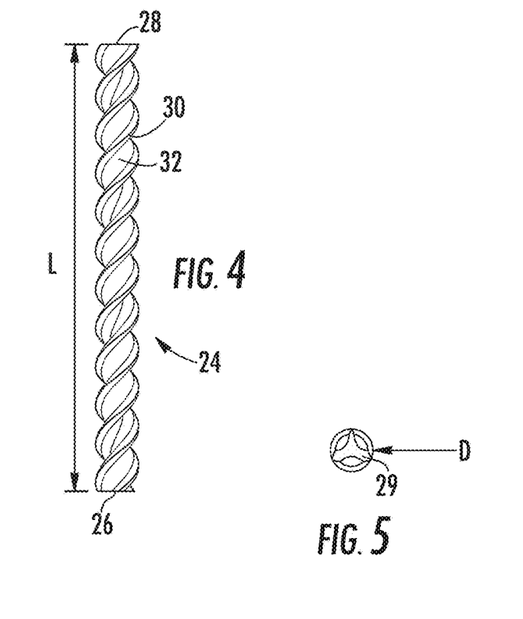
FIG. 4 is a side view of the reamer.
FIG. 5 is an end view of the reamer of FIG. 4.
Figure 6:
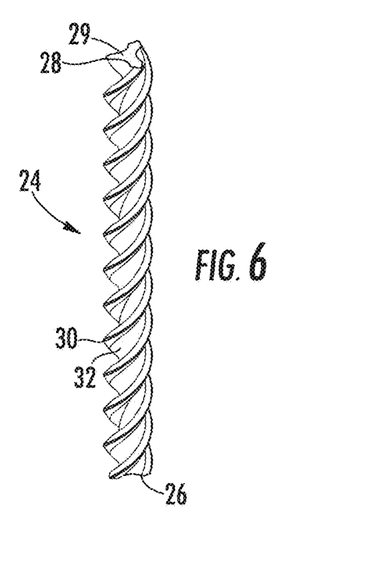
FIG. 6 is a side view of an alternative embodiment of the reamer.

FIGS. 4-6 show the reamer of the exemplary embodiment removed from the hollow body of the needle. FIG. 4 shows that the reamer has three flutes 32 and three lands 30. FIG. 4 shows the reamer has a length L from the distal end to the proximal end. FIG. 5 shows the reamer has an outer diameter D defined by the lands 30 when viewed from the distal end 28 of the reamer.

In particular, it has been found that a 4 FL. REAMER, 60 degree helix, 0.0240×0.250" long, 0.008" depth is a suitable structure for creating this turbulence. For this reamer, the length L is 0.250" and the diameter D is 0.024". It should be understood that this is just one example of the type and configuration of reamer than can be used in the present invention. For example, the shape and configuration of the micro nozzle insert reamer 24 can be changed, as in FIG. 6 which has a different thread pitch, to create different levels and type of turbulence to provide different color signatures when visualized on an ultrasound machine using the Doppler feature.

Although the exemplary embodiment includes a beveled tip 20 on the hollow body 12, other tip geometries are possible. For example, the needle could have a square tip. The tip would then have a tip edge having a circular outer profile that defines a tip face that is located in a plane that is perpendicular to the longitudinal axis of the hollow body of the needle.

The needle may be made of various materials, including plastic and metal. The needle of the exemplary embodiment is an insulated needle for use with an ultrasound device, though it is also possible to use non-insulated needles.

The user may be provided with needles for use with a previously purchased ultrasound machine, or the needles of the present invention may be provided to a user along with an ultrasound machine and a color display. The needles can be configured for single use.

Still further, the turbulence inducing member 24 may be of any configuration that induces turbulent flow of fluid when such fluid passes thereover and thereabout when being injected through the needle and out through the needle tip 20. While a helical fluted reamer 24 is preferred, other profiled surfaces may be employed or other structures (not shown). For example, spheres may be positioned in the needle to induce the required turbulence in the fluid.

Figure 7:
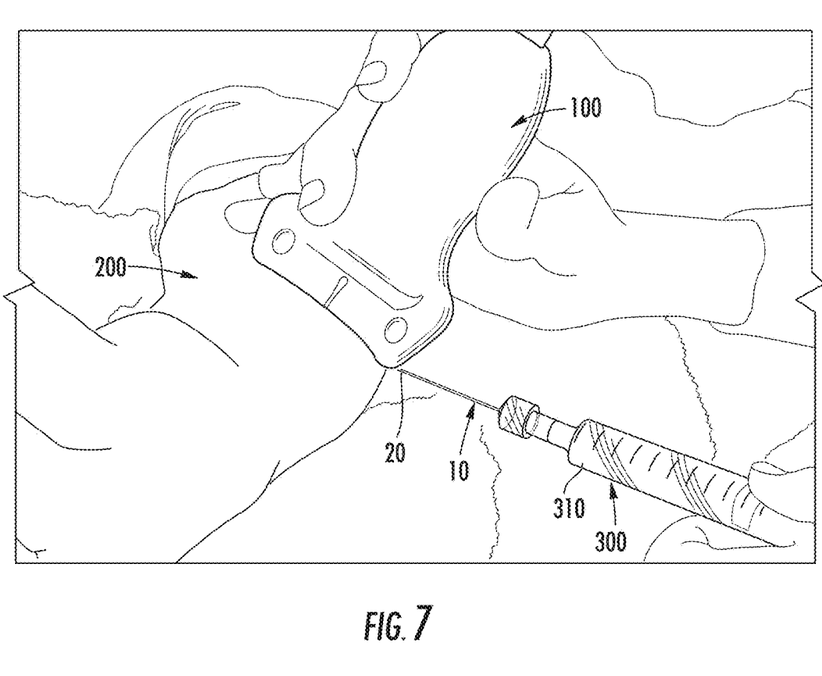
FIG. 7 is a perspective view of a user operating an ultrasound transducer and preparing to insert the needle into an arm of a patient.

FIG. 7 shows a perspective view of a user operating an ultrasound transducer 100 and preparing to insert the needle 10 into an arm 200 of a patient. The needle 10 of the present invention is secured to and extending from a syringe 300. The syringe has a chamber 310 containing fluid to be delivered to the patient's arm. The method of the present invention allows the user to position the needle 10 of the present invention for proper administration of the fluid (such as an anesthetic) to the patient.

The user first identifies a region of interest in the body or other living tissue in which to insert the needle. Within the region of interest, the user identifies a target location where the tip of the needle should be located. For example, an anesthesiologist or a physical medicine doctor can identify a nerve plexus in an area of the patient's body where tissue needs to be numbed, where the patient needs to be prepared for surgery, where pain needs to be reduced post-operatively, or where pain needs to be reduced in daily life. The body area of the patient may be an area such as the abdomen, an arm, a leg, a shoulder, a knee, an elbow, or another body part. Successful placement of the tip will place the tip substantially near the target location so that the proper dose of the fluid is directed to the target location, and so that the user avoids damaging surrounding tissue in the patient with the needle tip.

The user activates an ultrasound device that has a color display and color Doppler feature for viewing the output of the ultrasound machine. In the case of an ultrasound device having a handheld transducer, the user positions the transducer over the region of interest, and views the color display.

Then the user inserts the needle of the present invention into the patient, attempting to place the needle tip adjacent to the target location in the region of interest. When the user causes fluid to flow through the hollow body of the needle and the turbulence inducing member, the resulting turbulent flow of the fluid is visible in color on the color display of the ultrasound machine when the color Doppler feature is enabled. The user observes the location of this turbulent flow of fluid, and can thereby at least substantially determine the location of the tip of the needle. In particular the direction of the flow of the viewed color portions is a further indicator of the location of the tip of the needle. It can also be possible for the user to determine the rotation of the bevel tip of the needle. The user also observes anatomy of the patient nearby the needle. The user can adjust the angle of the needle and the depth of the needle within the patient to locate the turbulent flow, and thus the tip of the needle, appropriately within the patient's body.

FIGS. 8A-8D show sequential screen captures from a color display of an ultrasound machine, in accordance with the present invention, showing the output therefrom. As fluid is directed through the needle and out of the tip, the color display of the ultrasound machine shows a "cloud" or a jet-like flame that shows where the fluid, such as medicine, water, saline, and the like, is going immediately after it exits the needle tip. It is critical for an anesthesiologist to know where the medication is going, and using the color display and the needle of the present invention thus allows the user to identify the needle tip and the flow of the medicine being injected.

Figure 8A:
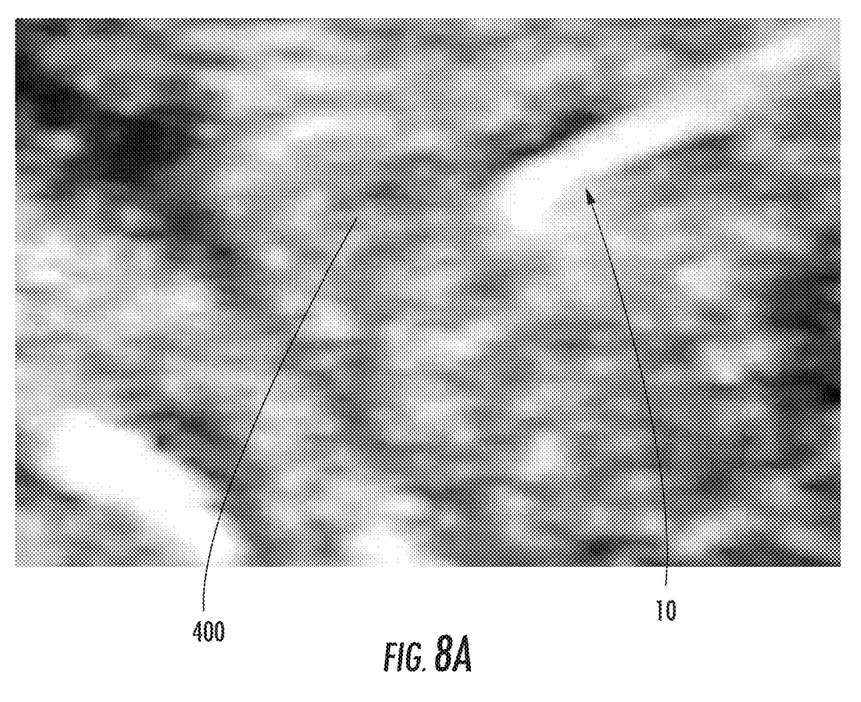
FIG. 8A shows an ultrasound image of a needle being inserted into the tissue of the patient, prior to injection of media, with no turbulent fluid exiting the needle tip.

FIG. 8A shows the tip of a needle 10 inserted into the tissue 400 of the patient, with no turbulent fluid exiting the needle tip 10. Although some color appears slightly visible, the screen capture appears as mostly black and white and gray regions.

Figure 8B:
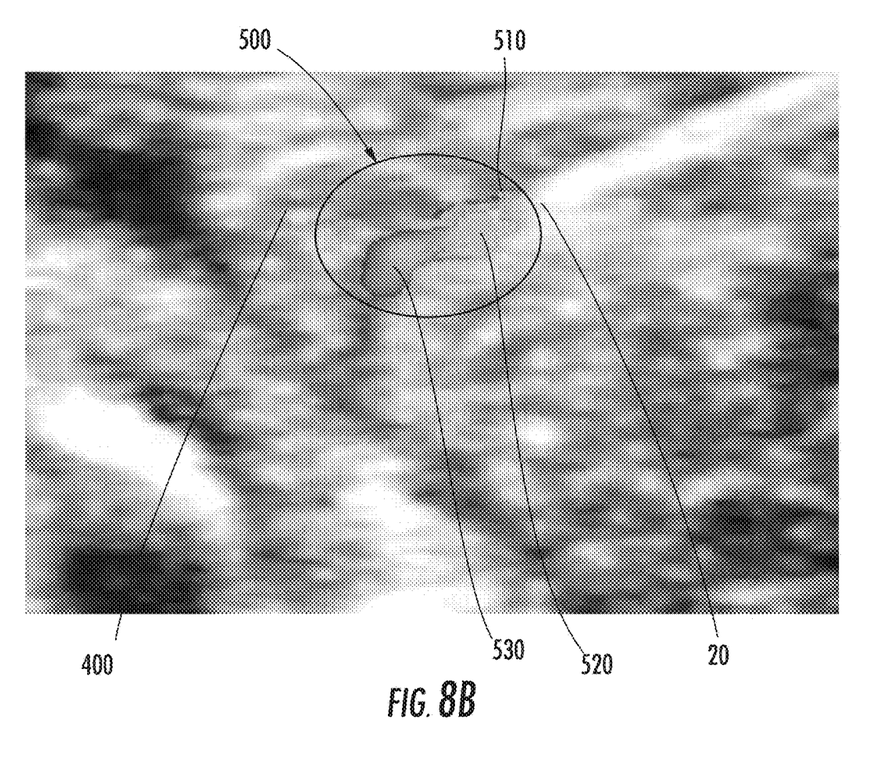
FIG. 8B shows an ultrasound image of the needle with fluid being injected through the needle tip with turbulent flow of fluid media from the tip thereof thereby identifying the location of the tip of the needle.

FIG. 8B shows an image captured shortly after fluid has been caused to exit the needle of the present invention. A small area of turbulent flow 500 is visible in color adjacent to the tip of the needle. In FIG. 8B, an area 510 of red, for example, of turbulent flow appears adjacent to the tip 20. A blue area of turbulent flow appears further from the tip, with a lighter blue area 520 adjacent to the tip, and a darker blue area 530 in the fluid that has advanced further from the tip. The tissue of the patient and the needle appear substantially in gray, black, and white. Therefore, the turbulent flow of the fluid is immediately visible to the user in color, and the tip of the needle, which appears in white, can be more easily distinguished from other substantially white areas within the patient's body.

Figure 8C:
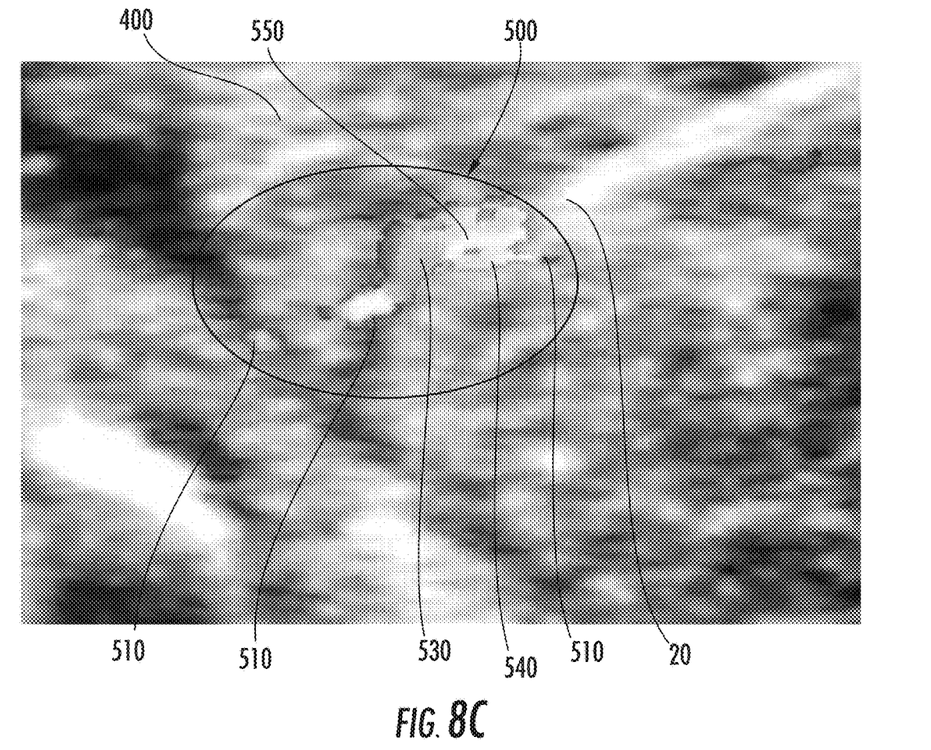
FIG. 8C shows a further ultrasound image of the needle with more fluid being injected through the needle tip and exhibiting additional turbulent flow.
Figure 8D:
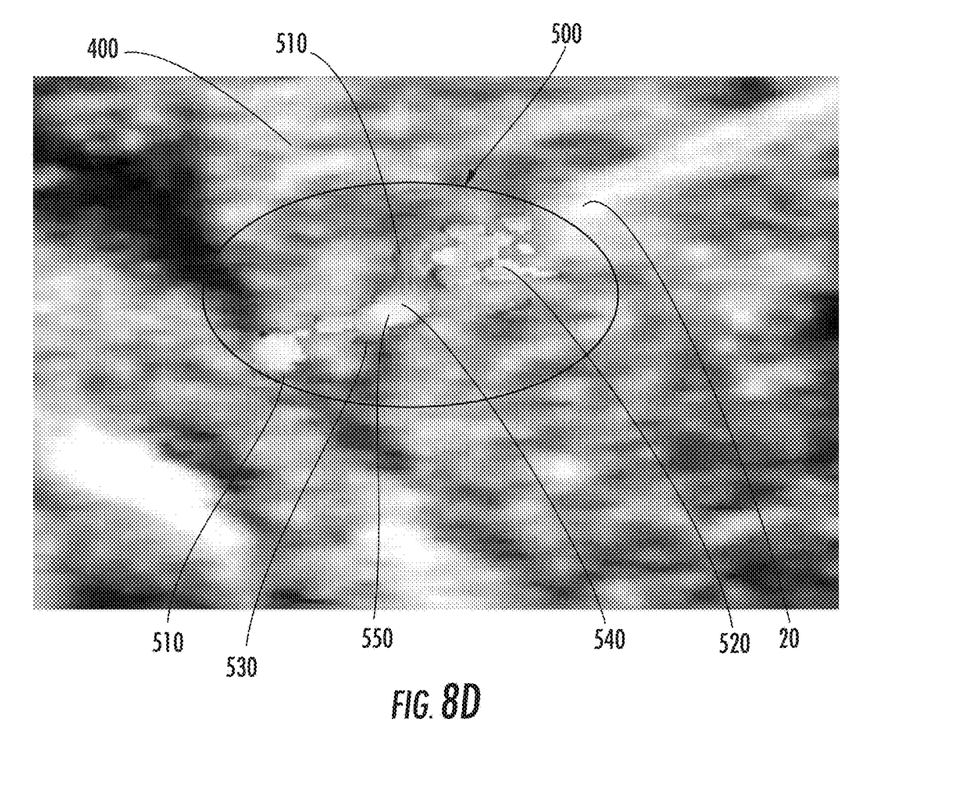
FIG. 8D shows yet a further ultrasound image of the needle with even more fluid being injected through the needle tip and exhibiting still additional turbulent flow.

As the turbulent flow continues over time, the color areas further develop. FIG. 8C shows turbulent flow in color areas such as red areas 510, yellow areas 540, blue areas 530, and white areas 550. The white areas of the turbulent flow are distinguishable from other white areas on the display by the colorfully displayed regions of turbulent flow surrounding them. FIG. 8D shows a third frame in the time sequence, with red being more pronounced in the displayed image of turbulent flow.

While the screen captures are useful for showing the tip location, the real time video is even more useful for a user of the needle. As the color areas develop, the user can see the point at which they form and from where they come, which is adjacent to the needle tip 20. Thus, the tip 20 of the needle 12 can be accurately determined.

Figures such as these screen captures can be used to prove to an insurance company that ultrasound was used, and that the medication was injected in the desired area.

The needle itself need not be echogenic, but it is possible to include echogenic features on the hollow body of the needle. Regardless, the primary echogenic benefit for determining tip location would be from the turbulent flow exiting the needle tip.

The helical path need not be formed by a reamer. It is possible to form the helical path by inserting other structures having helical grooves into the hollow body of the needle. Alternatively, the turbulence inducing member and hollow body of the needle may be manufactured as an integral piece.

Still further, it should be understood that any type of structure could be used at the needle tip to create the needed turbulence at the tip so that the needle can be seen in color on the ultrasound. For example, instead of a reamer configuration, micro balls in the needle and other structures can be used. The micro balls would be contained within the flow path of the needle, and would disrupt laminar flow through the hollow body of the needle. Thus, any means of inducing turbulence via a needle can be included, such as that shown in the figures and described herein.

Thus, the needle assembly of the present invention shows the needle tip and fluid injection in color. This allows more accurate needle placement, avoiding injury to neighboring structures, and allows successful needle placement for delivery of the medication or other fluid. The cost should be comparable to a standard needle.

While the needle assembly of the present invention is preferably made of plastic, it may be made out of any material that is medical grade and suitable for surgery.

It can therefore be seen that the present invention provides better visualization of the needle to achieve more accurate needle placement by inducing turbulence at the tip of the needle and viewing it by an ultrasound machine using the Doppler feature. The present invention helps avoid injury to neighboring structures, and helps allow more successful needle placement. Additionally, the present invention provides an improved needle that has a cost comparable to a standard needle. Furthermore, the invention provides a needle that is for single patient use and disposable. For these reasons, the instant invention is believed to represent a significant advancement in the art, which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A needle for use with an ultrasound machine to visualize the location thereof, the needle comprising:
   a main body having a proximal end and a distal open end, the main body being tubular thereby defining a media flow path therethrough and extending between the proximal end and the distal open end;
   the distal open end defining a tip;
   a media turbulence inducing member positioned within the media flow path and residing in the main body; and
   whereby media flowing through the media flow path of the main body passes by the media turbulence inducing member, comprising a non-linear surface, with the media turbulence member residing within the main body, and out through the tip is visible on an ultrasound machine.

2. The needle of claim 1, wherein the media flowing through the media flow path of the main body and out through the tip is visible on an ultrasound machine operating in color Doppler feature.

3. The needle of claim 1, wherein the media turbulence inducing member has helical fluted grooves.

4. The needle of claim 1, further comprising:
   a bevel formed on the tip, the bevel having a bevel angle between 30°-45°.

5. The needle of claim 1, wherein the main body further comprises an insulated outer surface.

6. The needle of claim 1, wherein the main body is formed from a material selected from the group consisting of a plastic and a metal.

7. A system for positioning a needle within a living body, the system comprising:
   an ultrasound machine; and
   a needle including a main body having a proximal end and a distal open end, the main body being tubular and defining a flow path therethrough; the needle defining a tip located at the distal end; and a media turbulence inducing member, comprising a non-linear surface, positioned within the flow path and located inside the main body;
   whereby media is configured to pass from the proximal end, through the flow path and past the media turbulence inducing member and out through the distal open end and out through the tip where turbulence of the media at the tip is greater than turbulence of the media at the distal end.

8. The system of claim 7, wherein the media turbulence inducing member has helical fluted grooves.

9. The needle of claim 7, further comprising:
a bevel formed on the tip, the bevel having a bevel angle between 30°-45°.

10. The needle of claim 7, wherein the main body has an insulated outer surface.

11. A method of locating a needle tip, the method comprising the steps of:
providing an ultrasound machine, the ultrasound machine having a color display for viewing output of the ultrasound machine;
providing a needle, the needle having a main body having a proximal end and a distal end, the main body being tubular and defining a flow path therethrough; the needle further having a tip located at the distal end;
positioning a media turbulence inducing member, comprising a non-linear surface, within the flow path and inside the main body;
inserting the needle tip into a body member;
activating the ultrasound machine;
positioning a transducer of the ultrasound machine over the region of interest;
routing media through the flow path, past the media turbulence inducing member, while the media turbulence inducing member is residing inside the main body and within the flow path, and out through the tip of the needle;
providing increased turbulence of the media exiting the tip compared to turbulence of the media at the distal end; and
observing color display portions of the ultrasound machine indicative of turbulent flow of media exiting the needle through the needle tip to thereby identify the location of the needle tip.

12. The method of claim 11, wherein the ultrasound machine is observes color display portions using a color Doppler feature.

13. The method of claim 11, wherein the media turbulence inducing member has helical fluted grooves.

* * * * *